United States Patent
Hsiung

(12) 
(10) Patent No.: US 6,716,638 B1
(45) Date of Patent: Apr. 6, 2004

(54) MEASURING CONDUCTING PATHS USING INFRARED THERMOGRAPHY

(75) Inventor: Chang-Meng Hsiung, Irvine, CA (US)

(73) Assignee: Cyrano Sciences Inc., Pasadena, CA (US)

(*) Notice: Subject to any disclaimer, the term of this patent is extended or adjusted under 35 U.S.C. 154(b) by 20 days.

(21) Appl. No.: 09/660,138

(22) Filed: Sep. 12, 2000

Related U.S. Application Data

(60) Provisional application No. 60/153,613, filed on Sep. 13, 1999.

(51) Int. Cl.[7] .................. G01N 25/20; G01N 25/18; G01N 27/00; G01N 21/00; G01N 21/75
(52) U.S. Cl. .................. 436/147; 436/149; 436/164; 422/83; 422/98; 136/201; 250/332; 73/23.2
(58) Field of Search .................. 422/98, 83; 436/147, 436/149, 164; 205/787, 777.5; 136/201; 250/332; 73/23.2

(56) References Cited

U.S. PATENT DOCUMENTS

| | | | | |
|---|---|---|---|---|
| 5,571,401 A | * | 11/1996 | Lewis et al. | 205/787 |
| 6,118,124 A | * | 9/2000 | Thundat et al. | 250/332 |
| 6,180,867 B1 | * | 1/2001 | Hedengren et al. | 136/201 |
| 6,244,096 B1 | * | 6/2001 | Lewis et al. | 73/23.2 |
| 6,319,724 B1 | * | 11/2001 | Lewis et al. | 436/149 |
| 6,331,244 B1 | * | 12/2001 | Lewis et al. | 205/777.5 |
| 6,438,497 B1 | * | 8/2002 | Mansky et al. | 702/22 |

* cited by examiner

Primary Examiner—Jill Warden
Assistant Examiner—Brian Sines
(74) Attorney, Agent, or Firm—Townsend and Townsend & Crew LLP

(57) ABSTRACT

A sensor array 120 contains two chemiresistor which generate a response 130 in the presence of an analyte. The response is detected using an infrared detector 135, such as an infrared camera The infrared detector 135 generates a thermographic image 140 for each sensor in the array. The thermographic image 140 contains a matrix of responses 150, 160 for each sensor.

6 Claims, 8 Drawing Sheets before exposure to analyte after exposure to analyte

MEASURING CONDUCTING PATHS USING INFRARED THERMOGRAPHY

CROSS-REFERENCE TO RELATED APPLICATIONS

This application claims priority to U.S. Provisional Patent Application No. 60/153,613, filed Sep. 13, 1999, the teachings of which are incorporated herein by reference in their entirety for all purposes.

FIELD OF THE INVENTION

In general, this invention relates to sensor arrays and in particular, to sensor array devices using an infrared detector to measure sensor response. The device is useful in monitoring the physical structure of sensors using infrared thermography.

BACKGROUND OF THE INVENTION

In general, electronic noses comprise an array of chemical sensing elements and a pattern recognition system. Electronic noses are designed to analyze complex vapors as they exist and produce a unique signature output. The sensor array is designed to respond to many different individual and complex compounds, analytes and vapors. The unique pattern enables the identification of an analyte of interest.

Following the trend that digitized images and sounds give machines the ability to see and hear, digitized odors give machines the ability to smell. Electronic noses are devices that can digitize odors. In certain instances, electronic noses are made of polymer composites and are based on a swell-to-smell mechanism (see, M. Lonergan, E. Severin, B. Doleman, S. Beaber, R. Grubbs, and N. Lewis, *Chemistry of Materials*, 8 (1996) 2298-2312; and A. Marquez, J. Uribe, and R. Cruz, *Journal of Applied Polymer Sciences*, 66 (1997) 2221–2232. Certain electronic noses can be easily manufactured into portable devices having affordable prices.

In spite of the advances made in the prior art, devices are needed that can detect analytes using an infrared detector. Moreover, devices and methods are needed that can monitor the manufactured quality of sensors. The present invention fulfills these and other needs.

SUMMARY OF THE INVENTION

In certain aspects, the present invention relates to a sensor array device for detecting an analyte in a fluid, comprising: an infrared detector operatively associated with each sensor wherein the detector measures a response in the presence of the analyte. Surprisingly, the inventor has discovered that the use of an infrared detector can monitor a distribution of responses, such as resistances, during exposure of the sensors to various vapors. The infrared detector can monitor changes in the distribution of resistances instead of merely detecting a single overall resistance. A distribution of responses is more indicative of an analyte compared to the overall resistance that is simply a summation of many different resistances. The present invention advantageously measures a matrix of resistances of the sensor array.

In another aspect, the present invention provides a method for monitoring the quality of a sensor, comprising: photographing the sensor with an infrared camera to generate a thermographic image; and analyzing the thermographic image thereby monitoring the quality of the sensor. In certain preferred aspects, the infrared thermographic image is especially useful in a manufacturing area such a quality control, or quality assurance, to monitor the manufacturing quality of sensor arrays.

In yet another aspect, the present invention provides methods for quantitatively predicting the response of the sensor based on its physical structural parameters. Preferably, sensors with a good topographical distribution of polymer(s) are used in the sensor array devices.

In still yet another embodiment, the present invention provides a method for identifying the conducting path of a sensor, comprising: photographing the sensor with an infrared camera to generate a thermographic image; and analyzing the thermographic image thereby identifying the conducting path of the sensor.

In other embodiments, a computer program product is provided that calculates the uniformity of the thermograph, which are generated by the infrared detector.

Numerous advantages are achieved using the present invention over conventional systems. For example, the present system provides enhances resolution of the sensor system. This feature allows unparalleled detection and identification of analytes in an environment. The sensor system of the present invention allows for enhanced resolution that ensures fewer incorrect identifications compared to conventional detectors.

The foregoing embodiments as well as other features and advantages of the present invention will be more apparent when read with the accompanying drawings and detailed description which follows.

DETAILED DESCRIPTION OF THE INVENTION AND PREFERRED EMBODIMENTS

I. Devices

In certain aspects, the present invention relates to a sensor array device for detecting an analyte in a fluid, the device comprises: an infrared detector operatively associated with each sensor wherein the detector measures a response in the presence of the analyte. In certain aspects, the infrared detector can produce a distribution of responses, such as resistances, during exposure of the sensors to various fluids. As used herein the term "fluid" means vapors, gases, liquids and solid materials. The infrared detector can measure changes in the distribution of resistances instead of a single overall resistance or a summation of resistances. The infrared detector is preferably an infrared camera. A distribution or matrix of responses, such as resistances, is more indicative of the identity of the analyte. A distribution of responses is displayed as a matrix (e.g., 256×256 pixels). Preferably, the distribution is displayed as a thermographic image.

It has surprisingly been discovered that the conducting paths in sensors, preferably sensors based on polymer composites, can be identified by applying a voltage to the sensor and thereafter capturing a thermographic image of the sensor using an infrared camera. Since the electrical energy released from the sensor is in reciprocal proportion to the resistance in a conducting path across the sensor, the low resistance paths (i.e., conducting paths) are heated and show higher temperatures. The thermographic image of the electrically heated sensor is then captured by a microscopic infrared camera and the distribution of the conducting paths are depicted by the high temperature regions in the thermographic image.

Prior to the advent of the present invention, the resistance of chemiresistor such as polymer-based chemiresistor, was generally measured by applying a constant voltage across the sensor and measuring the overall current that passes through the sensor (i.e., the summation response). Only a single value of resistance that characterizes the whole sensor can be measured. Unlike the single sensor-single response paradigm, using the present invention it is possible to measure an entire distribution or matrix of resistances, such as 256×256 values, in each sensor area. This matrix response paradigm is preferable because a more accurate identification of the analyte can be determined.

Figure 1:
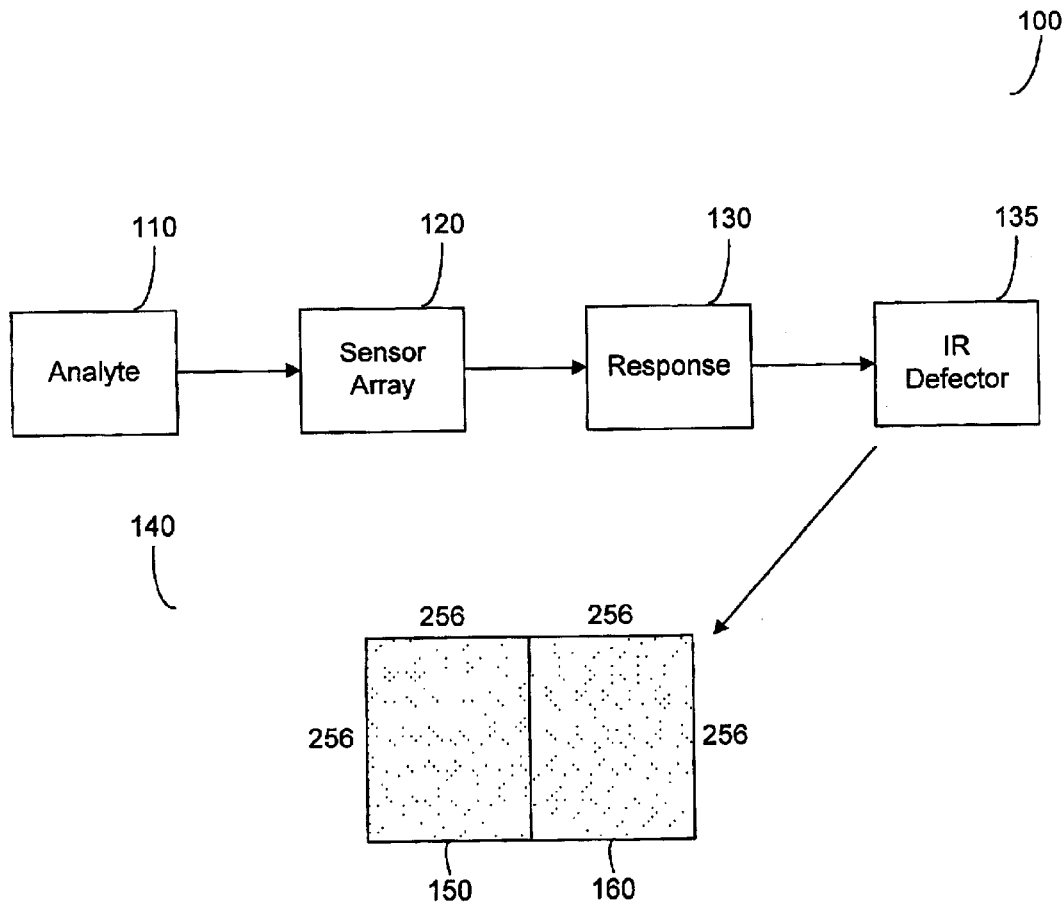
FIG. 1 illustrates a block diagram of the present invention.

FIG. 1 illustrates a block diagram 100 of the present invention. This block diagram is merely an illustration and should not limit the scope of the claims herein. One of ordinary skill in the art will recognize other variations, modifications, and alternatives.

Block diagram 100 shows a sensor array 120 responding to an analyte 110. A wide variety of sensor types can be used in the present invention. Preferably, the sensors are polymer-based sensors, such as those describe in U.S. Pat. No. 5,571,401 incorporated herein by reference. In this illustrative embodiment, sensor array 120 contains two chemiresistor which generate a response 130 in the presence of an analyte. The response is detected using an infrared detector 135, such as an infrared camera The infrared detector 135 generates a thermographic image 140 for each sensor in the array. The thermographic image 140 contains a matrix of responses 150, 160 for each sensor. In one embodiment, matrix 140 contains 256×256 pixels of resolution, responsive to both sensors in the array. In another embodiment, each sensor generates a matrix 150, 160, of resistances, or 256×256 pixels of resolution for each sensor in the array. As such, in certain embodiments, the present invention relates to a device for detecting analytes in a fluid comprising an array of sensors; and a detector capable of detecting a distribution of responses from the analyte. Preferably, a matrix of responses is detected.

Figure 2:
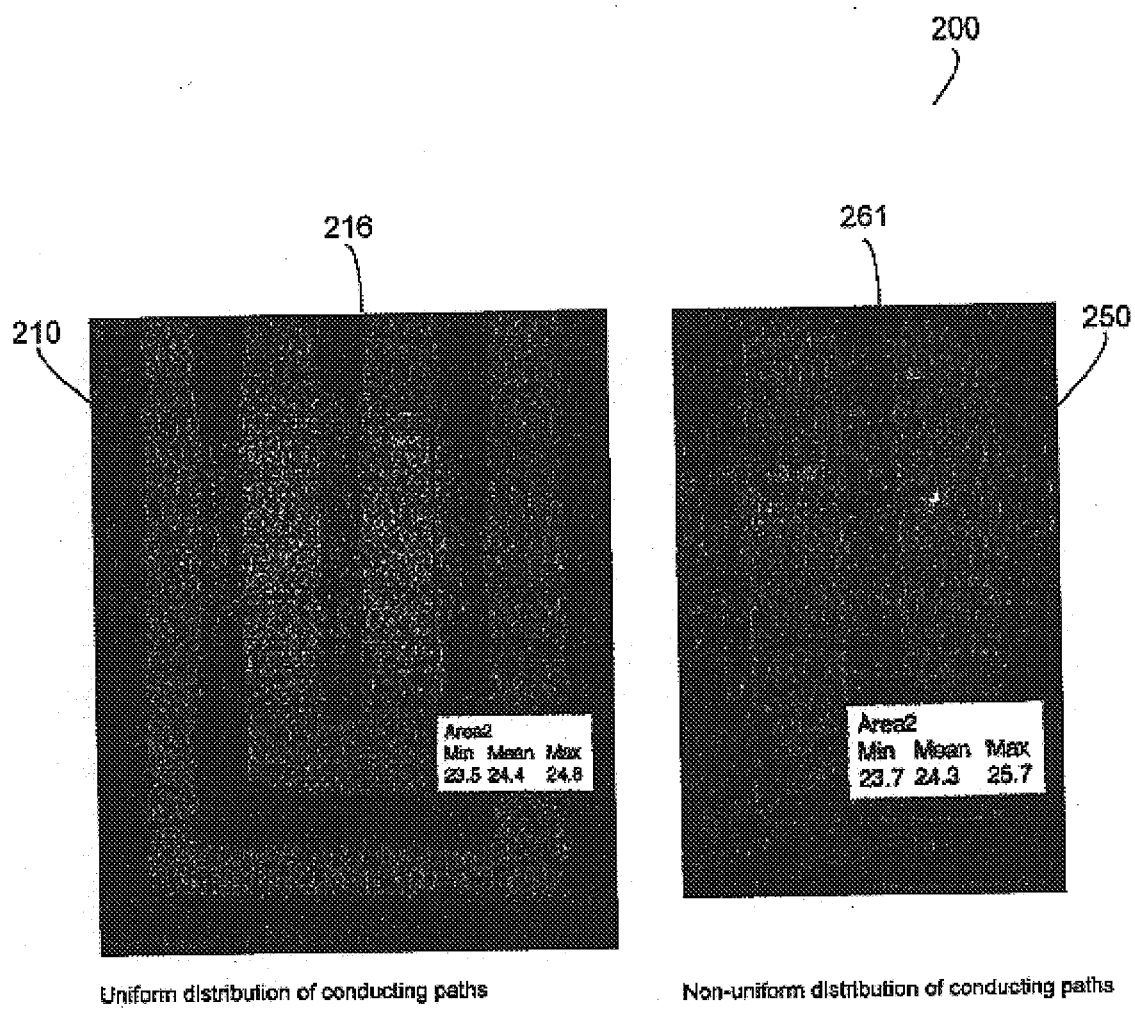
FIG. 2 illustrates sensor quality monitoring using a device and method of the present invention wherein the sensor has uniform distribution of conducting paths and non-uniform distribution of conducting paths.

FIG. 2 illustrates a representation of a distribution of conducting paths 200 of the present invention. The diagrams are merely an illustration and should not limit the scope of the claims herein. One of ordinary skill in the art will recognize other variations, modifications, and alternatives.

As shown therein, in sensor 210, there is a uniform distribution 216 of conducting path in the sensor. Sensor 261 shows a non-uniform distribution 250 of conducting paths in the sensor. Thus, the present invention provides a detailed description (e.g., with 256×256 pixels of resolution) of the distribution of resistance in a sensor. In certain aspects, the infrared detector output is useful as a quality control tool for identifying non-uniform hot spots in the sensor area. Moreover, additional data is extractable from the matrix about the analyte of interest. With this additional resolution of data, a more robust analysis of analyte identification is obtained The devices and methods of the present invention can identify a wide range of analytes. Suitable analyte include, but are not limited to, alkanes, alkenes, alkynes, dienes, alicyclic hydrocarbons, arenes, alcohols, ethers, ketones, aldehydes, carbonyls, carbanions, polynuclear aromatics, heterocycles, organic derivatives, biomolecules, microorganisms, fungi, bacteria, microbes, viruses, metabolites, sugars, isoprenes and isoprenoids, fatty acids and their derivatives. In certain preferred aspects, microorganism marker gases are detectable. These marker gases are indicative of certain medical conditions, such as diabetes, halitosis, lung cancer, etc.

In certain aspects, the device and methods of the present invention can be used in the medical applications disclosed in WO 99/66304, published Dec. 23, 1999 and incorporated herein by reference. As disclosed therein, the sensors can be used for detecting or diagnosing, for example, infections, lung cancer, oral infections and halitosis using a breath sample of a mammal. The methods can also be used for other medical applications, such as those involving the detection of marker gas(es) in mammalian breath as well as odors from potentially infected areas of the skin.

Without being bound by any particular theory, in operation, it is believed that the infrared detectors of the present invention use the following principles. According to Ohm's law, when a constant voltage is applied across a parallel array of resistors, the electrical energy released from each resistor is in reciprocal proportion to the resistance of it. As shown in Equation 1:

$$P = E/t = \frac{V^2}{R} \qquad 1$$

wherein P is power, E is energy, t is time of applying voltage, V is voltage, and R is resistance. This electrical energy is then used to heat up the sensor area as shown in Equation 2:

$$E = \int Cp \times M \times \alpha T \, dxdy \qquad 2$$

where M is Mass

M=area×thickness (τ)×density(ρ)

Assuming constant thickness, density, and Cp, then energy is shown as in Equation 3:

$$E = \rho \cdot Cp \cdot \tau \cdot \sum_{i,j} \Delta T_{i,j} \qquad 3$$

Thus, the following equation describes the relationship between the overall resistance of the sensor and the temperature increase at each pixel area in the sensor (Equation 4):

$$\frac{1}{R} = \left[\frac{\rho \cdot Cp \cdot \tau}{t \cdot V^2}\right] \times \sum_{i,j} \Delta T_{i,j} \qquad 4$$

Moreover, in certain aspects, the present invention monitors changes in the distribution of resistance during exposure of the sensors to various vapors. In this aspect, detailed information is provided about the response of the sensor array and performance of the sensors and possible exploration of the sensing mechanism of the electronic nose.

The sensor array device of the present invention can be used in a wide variety of applications. Suitable applications include, but are not limited to, environmental toxicology, remediation, biomedicine, material quality control, food monitoring, agricultural monitoring, heavy industrial manufacturing, ambient air monitoring, worker protection, emissions control, product quality testing, oil/gas petrochemical applications, combustible gas detection, $H_2S$ monitoring, hazardous leak detection, emergency response and law enforcement applications, explosives detection, utility and power applications, food/beverage/agriculture applications, freshness detection, fruit ripening control, fermentation process monitoring and control, flavor composition and identification, product quality and identification, refrigerant and fumigant detection, cosmetic/perfume applications, fragrance formulation, chemical/plastics/pharmaceuticals applications, fugitive emission identification, solvent recovery effectiveness, hospital/medical applications, anesthesia and sterilization gas detection, infectious disease detection, breath analysis and body fluids analysis.

II. Sensor Arrays

The devices and methods of the present invention include an array of sensors and, in certain instances, the sensors as described in U.S. Pat. No. 5,571,401 are used. Sensors suitable for detection of analytes associated with agricultural products include, but are not limited to, surface acoustic wave (SAW) sensors; quartz microbalance sensors; conductive composites; chemiresitors; metal oxide gas sensors, such as tin oxide gas sensors; organic gas sensors; metal oxide field effect transistor (MOSFET); piezoelectric devices; infrared sensors; sintered metal oxide sensors; Pd-gate MOSFET; metal FET structures; metal oxide sensors, such as a Tuguchi gas sensors; phthalocyanine sensors; electrochemical cells; conducting polymer sensors; catalytic gas sensors; organic semiconducting gas sensors; solid electrolyte gas sensors; temperature sensors, humidity sensors, piezoelectric quartz crystal sensors; and Langmuir-Blodgett film sensors.

In a preferred embodiment, the sensors of the present invention are disclosed in U.S. Pat. No. 5,571,401, incorporated herein by reference. Briefly, the sensors described therein are conducting materials and nonconducting materials arranged in a matrix of conducting and nonconducting regions, or a conducting/nonconducting regions. The nonconductive material can be a nonconducting polymer such as polystyrene. The conductive material can be a conducting polymer, carbon black, an inorganic conductor and the like. The sensor arrays comprise at least two sensors, typically about 32 sensors and in certain instances 1000 or more sensors. The array of sensors can be formed on an integrated circuit using semiconductor technology methods, an example of which is disclosed in PCT Patent Application Serial No. WO 99/08105, entitled "Techniques and Systems for Analyte Detection," published Feb. 19, 1999, and incorporate herein by reference. Another preferred sensor is disclosed in WO 99/27357 entitled "Materials, Method and Apparatus for Detection and Monitoring Chemical Species," published Jun. 3, 1999.

Preferably, the sensor arrays of the present invention comprise at least one sensor selected from the following group of sensors, inorganic metal oxide semiconductors such as tin-oxide based sensors, organic conducting polymers such as polymers of pyrrole and aniline, mass sensitive piezoelectric sensors such as bulk acoustic wave and surface acoustic wave sensors and nonconducting/conducting regions sensors.

As will be apparent to those of skill in the art, the sensors making up the array of the present invention can be made up of various sensor types as set forth above. For instance, the sensor array can comprise a conducting/nonconducting regions sensor, a SAW sensor, a metal oxide gas sensor, a conducting polymer sensor, a Langmuir-Blodgett film sensor, and combinations thereof.

In certain embodiments, the temporal response of each sensor (response as a function of time) is recorded and can be displayed, preferably thermographically displayed. Various responses include, but are not limited to, resistance, impedance, capacitance, inductance, magnetic, optical, etc. The temporal response of each sensor can be normalized to a maximum percent increase and percent decrease that produces a response pattern associated with the exposure of the analyte. By iterative profiling of known analytes, a structure-function database correlating analytes and response profiles is generated. Unknown analytes can then be characterized or identified using response pattern comparison and recognition algorithms. Accordingly, analyte detection systems comprising sensor arrays, an infrared measuring device for detecting responses across each sensor, a computer, a display such as a thermographic display, a data structure of sensor array response profiles, and a comparison algorithm(s) or comparison tables are provided.

In certain aspects, the sensor array devices of the present invention are used in high throughput screening of catalysts, pharmaceuticals and agricultural chemicals. Thus, the devices further comprise robotic armature for high throughput assay screening. In general, these robotic systems include automated workstations like the automated apparatus developed by Takeda Chemical Industries, LTD. (Osaka, Japan) and many robotic systems utilizing robotic arms (Zymate II, Zymark Corporation, Hopkinton, MA.; Orca, Hewlett-Packard, Palo Alto, Calif.), which mimic the manual operations performed by a technician. The nature and implementation of modifications to these devices (if any) so that they can operate will be apparent to persons skilled in the relevant art.

III. Pattern Recognition Algorithms

The device and methods of the present invention optionally comprise pattern recognition algorithms. Many of the algorithms are neural network based algorithms. A neural network has an input layer, processing layers and an output layer. The information in a neural network is distributed throughout the processing layers. The processing layers are made up of nodes that simulate the neurons by its interconnection to their nodes.

In operation, when a neural network is combined with a sensor array, the sensor data is propagated through the networks. In this way, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In a preferred embodiment, the Fisher linear discriminant analysis (FLDA)

and canonical discriminant analysis (CDA) and combinations thereof are used to assess patterns in responses from the electronic noses of the present invention.

The operating principles of certain algorithms are disclosed in Shaffer et al., *Analytica Chimica Acta*, 384, 305–317 (1999). These algorithms include 1) Nearest neighbor (NN); 2) Mahalanobis linear discriminant analysis 3) Bayes linear discriminant analysis (BLDA); 4) Soft independent modeling of class analogy (SIMCA); 5) Artificial neural networks (BP-ANN); 6) Probabilistic neural networks (PNA); 7.) Learning vector quantitation (LVQ).

Other analyses suitable for identifying analytes and quantifying concentration include, but are not limited to, principal component analysis, Fischer linear analysis, neural networks, genetic algorithms, fuzzy logic, pattern recognition, and other algorithms. After analysis is completed, the resulting information is displayed on display or transmitted to a host computer.

In certain instances, a statistical metric is used as disclosed in WO 99/61902, published Dec. 2, 1999, and incorporated herein by reference in its entirety for all purposes. A method for distinguishing different odors or vapor is disclosed therein. The method steps include providing a plurality of d sensors in an array, each sensor having different electrical responses to different orders; exposing the sensors to first and second odors; generating first and second sets of data points from each of the sensors, each set corresponding to the first or second odor, each data point being represented by a vector in a d-dimensional space; determining an axis in the d-dimensional space, the axis having the property that projections of the data points onto the axis in the d-dimensional space have optimal separation; and resolving the first odor from the second odor by the separation.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

In practice, PCA compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a proportional constant. Another relationship between matrices is that they share principal components in common, but their eigenvalues differ. The mathematical technique used in PCA is called eigen analysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix. (see, *Advances in Multivariate Statistical Analysis*, p. 31–43, in A. K. Gupta (ed), Reidel, Boston; and Flury, B. (1988) *Common Principal Components and Related Multivariate Models*, Wiley, N.Y.). Commercially available statistical packages and software programs are available for performing principal component analysis (SAS Institute Inc., Cary, N. C., USA or www.sas.com).

Figure 3:
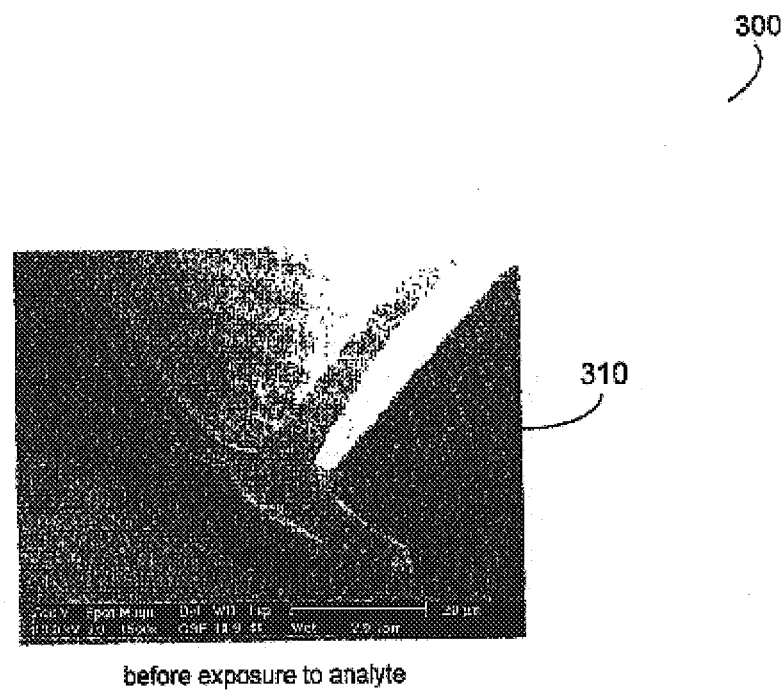
FIG. 3 illustrates a sensor in the absence and in the presence of analyte.
Figure 3:
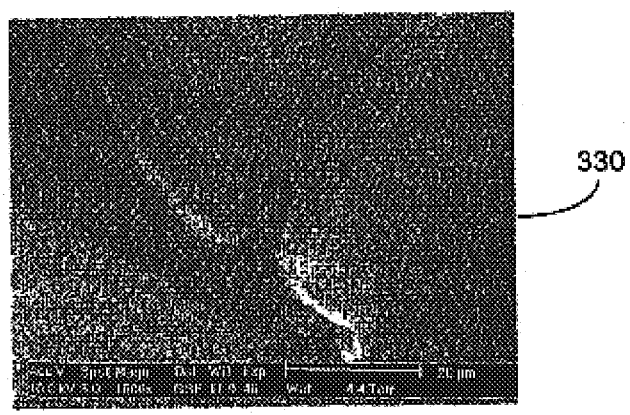

In another embodiment, a patterning mechanism is used. FIG. 3 illustrates a patterning mechanism 300 of the present invention. The are merely an illustration and should not limit the scope of the claims herein. One of ordinary skill in the art will recognize other variations, modifications, and alternatives.

As illustrated therein, the polymer(s) making up the sensor 310 before expose to analyte is in a relaxed state. After exposure to analyte, the polymer(s) making up the sensor "swells" into an unrelaxed state. In certain aspects, the "pattern" of swelling or sensor response can be used to make a determination or identification of the analyte. Using the pattern recognition algorithms discussed above, the "pattern" of the "polymeric swelling" can be used to identify the analyte. The sensor swells 330 (especially in the lateral directions) after it has been in contact with the analyte. Due to the lateral expansion of the polymer composite, the gaps between the three pieces of polymer composite are bridged after exposure to the analyte.

Figure 4:
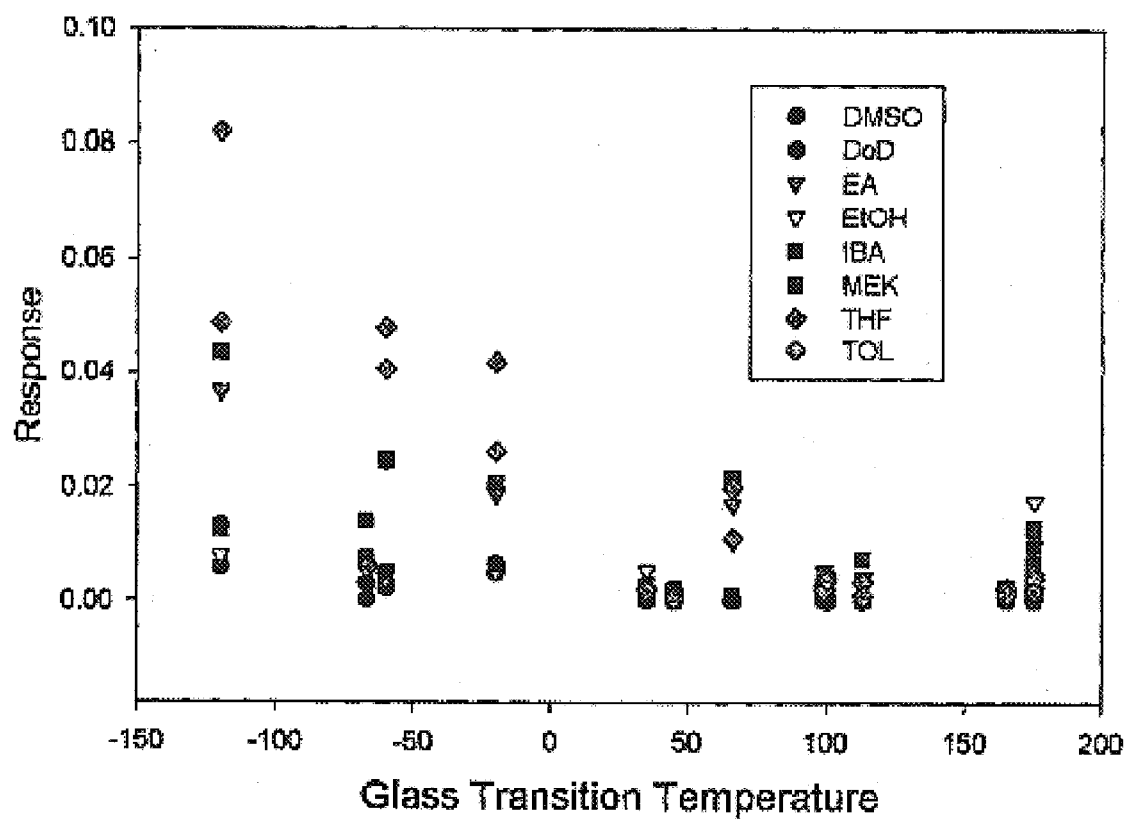
FIG. 4 illustrates the influence of the glass transition temperature of a polymer on the sensors' response.

FIG. 4 illustrates the influence of the glass transition temperature of the polymers on the sensors' response. As illustrated therein, polymers with lower glass transition temperatures show higher response to all the analytes. Thus, in certain aspects, it is advantageous to select softer polymers to generate larger response conditions for particular analytes. Polymers with lower glass transition temperatures show higher response to all the analytes.

IV. Computer Program Product

Figure 5:
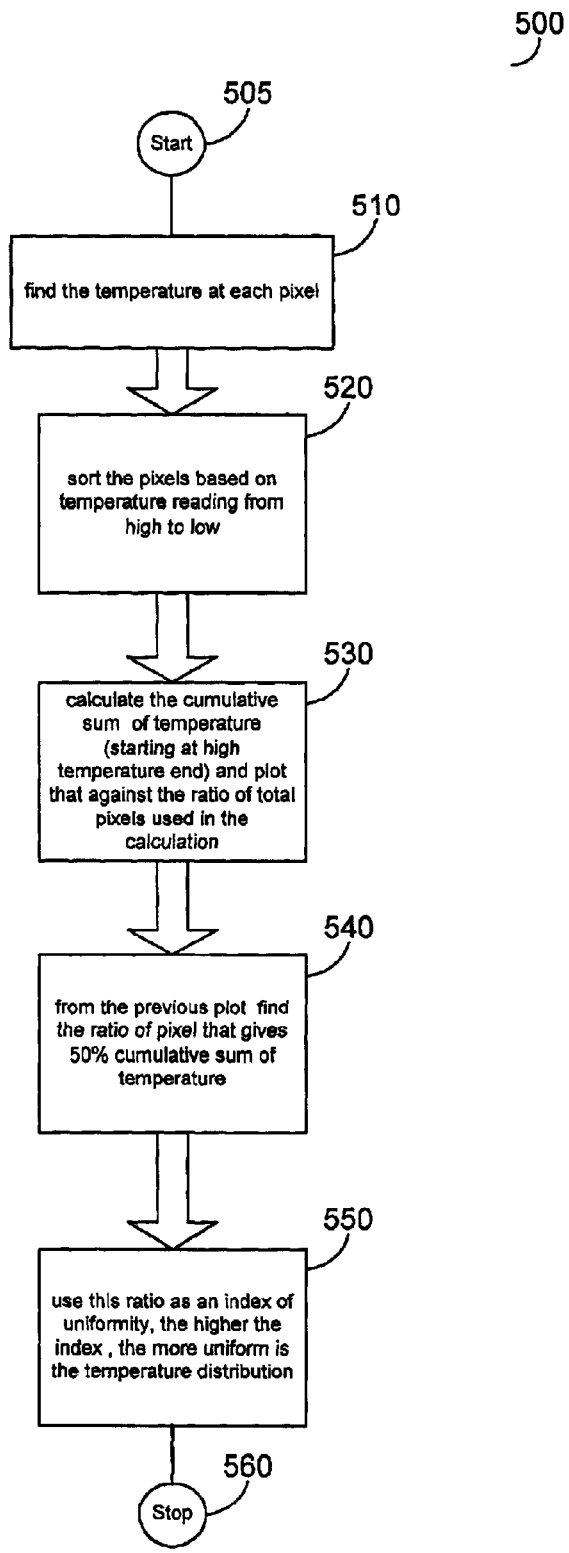
FIG. 5 illustrates a flow diagram of an embodiment of the present invention.

In certain aspects, the present invention provides a computer program product to calculate the uniformity of an infrared detector output, (e.g., thermograph). FIG. 5 illustrates a flow diagram 500 of a computer program product of the present invention. This is merely an illustration and should not limit the scope of the claims herein. One of ordinary skill in the art will recognize other variations, modifications, and alternatives.

In certain aspects, the computer program product of the present invention includes code for finding the temperature at each pixel of the output (e.g. thermograph) 510. The computer program product also includes code for sorting the pixels of the output based on temperature 520. Next, the computer program product further includes code for calculating the cumulative sum of temperature and plotting the cumulative sum against the ratio of total pixels 530. In step 540, the computer program product includes code for calculating the ratio of pixels that generates the 50% cumulative sum of temperature. The ratio in step 540 is thereafter used as an index of uniformity in step 550. The higher the index, the more uniform the temperature distribution.

Figure 6A:
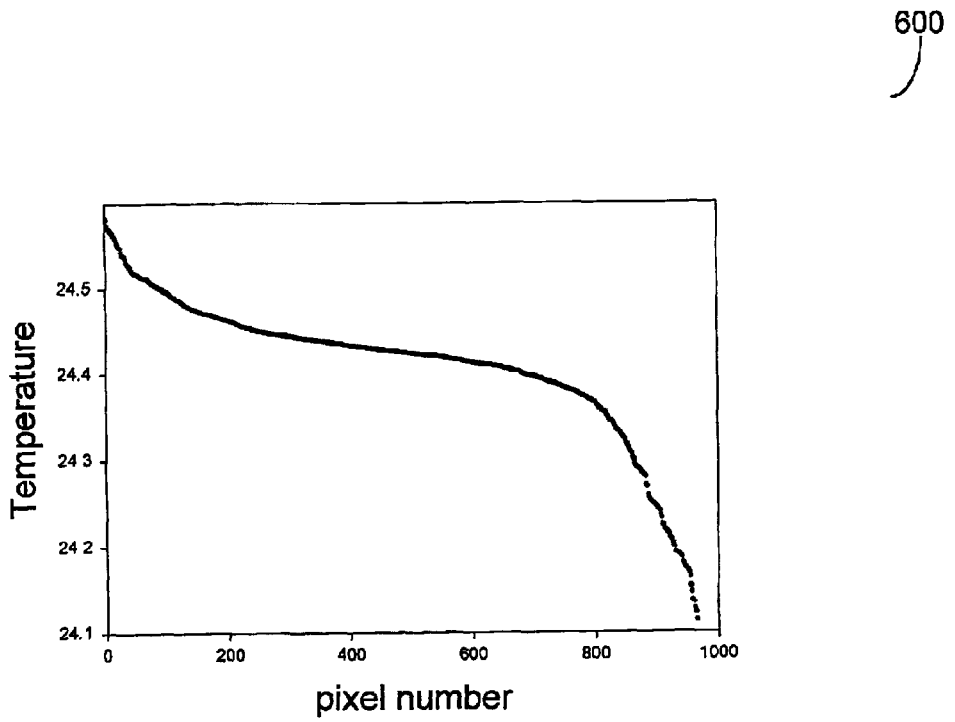
FIG. 6 Panel A–B illustrate embodiments of the uniformity calculation steps of the flow diagram in FIG. 5. Panel A depicts the sorting of the pixels according to their temperature reading in descending order and Panel B depicts calculating the cumulative integration of a distribution from the high temperature end.
Figure 6B:
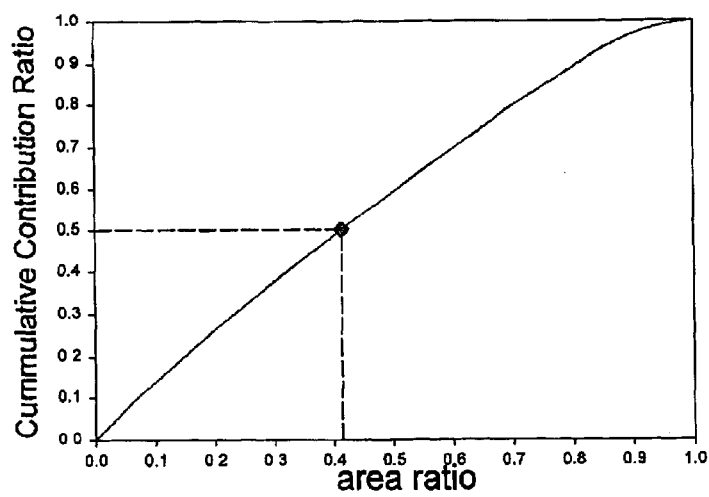

In operation, the uniformity of the distribution of the temperature in an IR thermograph can be quantified as follows: First, the pixels are sorted according to their a temperature reading in descending order as shown in FIG. 6A. Next, the cumulative integration of the distribution is calculated from the high temperature end, and rescaled by dividing the cumulative integration by the summation of all temperatures (ie. , the total area under the plot in FIG. 6A and the pixel number by the total number of pixels). The cumulative integration divided by the summation of all temperatures is shown in FIG. 6B. Thereafter, the computer code product finds the corresponding area ratio (uniformity factor) that gives the cumulative contribution ratio the value of 0.5. The purpose of this process is to find the percentage of the highest temperature pixels (area) that contribute to half of the total temperature. The ratio can then be used as a uniformity factor. For a perfectly uniform distribution, the uniformity factor is 0.5. FIG. 2, shows a sensor 216 having a uniformity factor of 0.413 and a sensor 261 having a uniformity factor equal to 0.231

While the invention has been described with reference to certain illustrated embodiments this description is not intended to be construed in a limiting sense. For example, the computer platform used to implement the above embodiments include 586 class based computers, Power PC based computers, Digital ALPHA based computers, SunMicrosystems SPARC computers, etc.; computer operating systems may include WINDOWS NT, DOS, MacOs, UNIX, VMS, etc.; programming languages may include C, $C^{++}$, Pascal, an object-oriented language, etc. Various modifications of the illustrated embodiments as well as other embodiments of the invention will become apparent to those persons skilled in the art upon reference to this description. In addition, a number of the above processes can be separated or combined into hardware, software, or both and the various embodiments described should not be limiting.

EXAMPLES

The following example is offered to illustrate, but not to limit the claimed invention.

Example

Experimental

Sensor Array Preparation: Thirty-two polymers with distinct solubility parameters were chosen, allowing the use of carbon black dispersions with various polymers. The appropriate amount of polymer solution is withdrawn and mixed with an appropriate amount of carbon black dispersion to obtain the desired dilution ratio. The dispersion is deposited by a spray method.

Characterization of Physical Structure Parameters: The glass transition temperatures of the polymers were measured by a Shimadzu Differential Scanning Calorimeter. The solubility parameters of polymers and analytes were found in the literature or calculated by a molecular modeling approach. Surface morphology of sensors in contact with analyte was examined by a Hitachi Environmental Scanning Electron Microscope. The thickness of sensors was measured by a Dektak surface profiler.

Results

Figure 7:
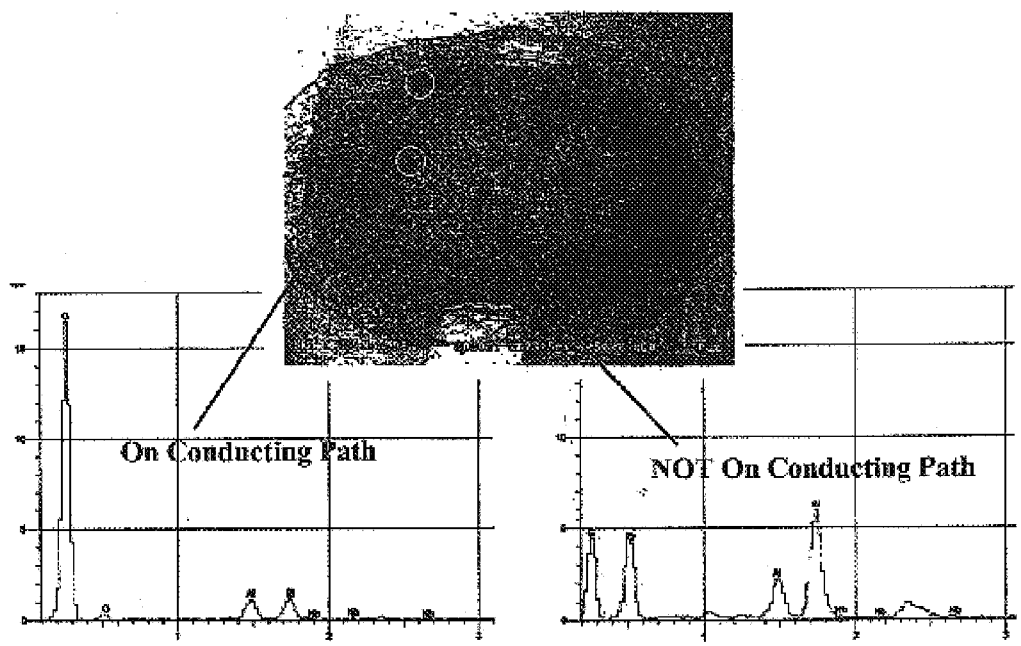
FIG. 7 illustrates an energy dispersive X-ray of a sensor deposited by an airbrush.

FIG. 7 illustrates an energy dispersive X-ray (EDX) 700 of a conducting/nonconducting regions sensor. The EDX is an attachment to the scanning electron microscope apparatus that was used. It is similar to an elemental analysis of the sensing material. The conducting path shows a higher carbon content (the conducing material region) compared to a path not on the conducting g region.

Figure 8:
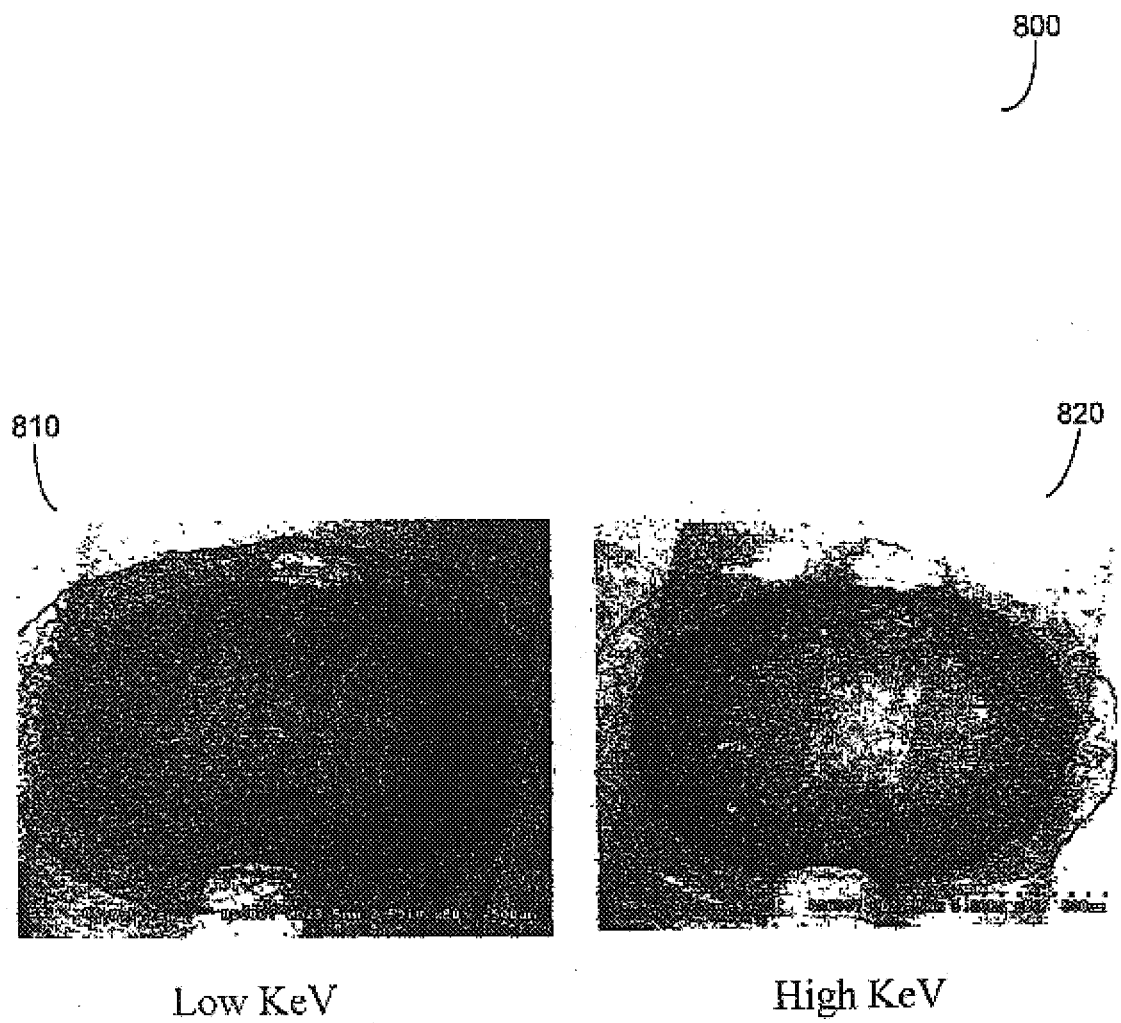
FIG. 8 illustrates an energy dispersive X-ray of a sensor deposited by airbrush at low KeV and high KeV.

In addition, FIG. 8 illustrates an energy dispersive X-ray (EDX) 800 of a conducting/nonconducting regions sensor. As shown therein, a low KeV EDX 810 shows the conducting paths in a donut shape topology. This donut shape topology is maintain even at higher KeV 820.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for assessing the uniformity in temperature distribution in regions of a sensor comprising a sensor array which comprise conduction paths, comprising:

applying a voltage to said sensor to cause said sensor to dissipate energy;

capturing an image of said sensor with an infrared camera to generate a thermographic image of said sensor while said sensor is dissipating energy;

identifying conduction paths in said sensor array as regions having a higher temperature than their surroundings;

calculating a measure of the uniformity of the temperature distribution of the image; and assessing the uniformity of the temperature distribution is said regions, using said measure, wherein a higher measure value corresponds with a more uniform temperature distribution.

2. The method according to claim 1, wherein at least one of said sensors in said array is a member selected from the group consisting of conducting/nonconducting sensors, bulk conducting polymer films, surface acoustic wave devices, fiber optic micromirrors, quartz crystal microbalances, dye impregnated polymeric coatings on optical fibers, sintered metal oxide sensors, phthalocyanine sensors, Pd-gate MOSFET devices, electrochemical cells, conducting polymer sensors, lipid coating sensors, metal FET structures, carbon black-polymer composites, micro-electro-mechanical system devices, micromachined cantilevers, and micro-opto-electro-mechanical system devices.

3. The method according to claim 2, wherein at least one of said sensors in said array is a conducting/nonconducting regions sensor.

4. A method for identifying the conducting path of a sensor comprising a sensor array, comprising:

applying a voltage to said sensor to cause said sensor to dissipate energy;

capturing an image of said sensor with an infrared camera to generate a thermographic image of said sensor while said sensor is dissipating energy; and identifying conduction paths in said sensor array as regions having a higher temperature than their surroundings.

5. The method according to claim 4, wherein said sensor is a member selected from the group consisting of conducting/nonconducting regions sensors, bulk conducting polymer films, surface acoustic wave devices, fiber optic micromirrors, quartz crystal microbalances, dye impregnated polymeric coatings on optical fibers, sintered metal oxide sensors, phthalocyanine sensors, Pd-gate MOSFET devices, electrochemical cells, conducting polymer sensors, lipid coating sensors, metal FET structures, carbon black-polymer composites, micro-electro-mechanical system devices, micromachined cantilevers, and micro-opto-electro-mechanical system devices.

6. The method according to claim 1 wherein said measure comprises a temperature uniformity factor comprising a ratio of regions in said image that contribute to a proportion of a cumulative sum of the temperatures.

* * * * *